United States Patent
Kawaguchi et al.

[11] Patent Number: 5,882,594
[45] Date of Patent: Mar. 16, 1999

[54] DEVICE AND METHOD FOR AUTOMATIC SAMPLE PRETREATMENT

[75] Inventors: Seiji Kawaguchi, Fujisawa; Toshiaki Kono, Shinnanyo; Hidechika Hayashi, Yokohama, all of Japan

[73] Assignee: Tosoh Corporation, Yamaguchi, Japan

[21] Appl. No.: 869,597

[22] Filed: Jun. 5, 1997

[30] Foreign Application Priority Data

Jun. 14, 1996 [JP] Japan ................................ 8-153866
Jul. 23, 1996 [JP] Japan ................................ 8-193324

[51] Int. Cl.$^6$ ................................................ G01N 35/02
[52] U.S. Cl. ........................... 422/64; 422/63; 422/65; 436/43; 436/47; 436/48; 436/49
[58] Field of Search ................... 422/63, 64, 65, 422/67, 100, 103, 104; 436/43, 147, 48, 49, 174, 179, 180

[56] References Cited

U.S. PATENT DOCUMENTS

| | | | |
|---|---|---|---|
| 5,051,238 | 9/1991 | Umetsu et al. | 422/64 |
| 5,384,093 | 1/1995 | Ootani et al. | 422/63 |
| 5,439,646 | 8/1995 | Tanimizu et al. | 422/64 |
| 5,472,669 | 12/1995 | Miki et al. | 422/63 |
| 5,587,129 | 12/1996 | Kurosaki et al. | 422/64 |
| 5,639,425 | 6/1997 | Komiyama et al. | 422/63 |

FOREIGN PATENT DOCUMENTS

92/05448  2/1992  WIPO .

Primary Examiner—Long V. Le
Attorney, Agent, or Firm—Nixon & Vanderhye

[57] ABSTRACT

An automatic sample pretreatment device is provided which is capable of conducting a series of treatments or reactions from pretreatment to measurement automatically in a short time by employing a separate reaction system from the reaction system for measurement. The automatic sample pretreatment device comprises a sample rack, a pretreatment vessel and a measurement vessel, a liquid dispenser, a first vessel-transfer apparatus having a vessel holder for holding and transferring the vessels, a pretreatment vessel feeding apparatus for feeding the pretreatment vessel to the vessel holder of the first vessel transfer apparatus, a measurement vessel feeding apparatus for feeding the measurement vessel to the vessel holder of the first vessel-transfer apparatus, a vessel discarding hole for discarding the vessel after use, a second vessel-transfer device for transferring the used vessel held at the vessel holder of the first vessel-transfer apparatus to the vessel discarding hole, an incubator equipped with a measurement device for measuring a sample, and a third vessel-transfer device for transferring the vessel held by the vessel holder of the first vessel-transfer apparatus to the incubator.

15 Claims, 3 Drawing Sheets

DEVICE AND METHOD FOR AUTOMATIC SAMPLE PRETREATMENT

BACKGROUND OF THE INVENTION

1. Field of the Invention

The present invention relates to an automatic sample pretreatment device of an automatic analysis apparatus for a specific component in a sample. The automatic sample pretreatment device is preferably integrated into the automatic analysis apparatus, and serves to dilute a sample and/or to cause a pretreatment reaction automatically prior to the measurement. Particularly, the present invention relates to an automatic pretreatment device for dilution or pretreatment reaction of a sample, integrated into a biochemical analysis apparatus such as an automatic immunoassay apparatus.

2. Description of the Related Art

Clinical diagnosis of some specific diseases is conducted by measurement of a specific substance in a body fluid such as blood. For example, immunoassay with an antibody for a specific substance, which can be conducted readily with relatively high sensitivity, is widely employed in clinical test nowadays.

In biochemical or immunological measurement, the sample is usually pretreated, prior to the measurement, for dilution of the sample containing a high concentration of the objective substance to bring the concentration to the analysis range of the measurement apparatus, or pretreated for improvement of measurement sensitivity or measurement precision by canceling the influence of a coexisting substance in the sample or activating the objective component. The reaction for the pretreatment includes heating treatment of the sample to denature protein in the sample or to inactivate or activate a specific component; and addition of a pretreatment reagent other than the measurement reagent. More specifically, in immunoassay of a protein-bonded low molecular component in a sample, the protein is denatured preliminarily by application of heat, or addition of an acid or alkali to dissociate the low molecular component from the protein, and subsequently the immunoassay is conducted.

As described above, the pretreatment including dilution, and pretreatment reaction including addition of a denaturing reagent, agitation, incubation, and addition of an neutralizing agent is conducted manually in most cases by taking a long time. Therefore, measurement of a large number of samples is time-consuming, troublesome, and less reproducible, disadvantageously.

Various methods are proposed to solve the above problems. In one method, a pretreatment reaction apparatus is provided separately. In another method, a sample and a pretreating reagent are allowed to react in a reaction cuvette of an automatic analysis apparatus, and subsequently a measurement reagent is added thereto to conduct measurement. By such a method, the pretreatment operation can be simplified, and the measurement reproducibility can be improved. However, the use of a separate pretreatment reaction device requires transfer of the sample to the measurement apparatus after the pretreatment reaction, producing another problem that the entire operation from the pretreatment to the measurement cannot be automated.

The above second method, in which a sample and a pretreatment reagent are introduced into a reaction cuvette of an automatic analysis apparatus to cause a pretreatment reaction, involves the problem that the practicable pretreatment reactions are limited. Further, in this method, the reaction cuvette for the pretreatment reaction is usually replaced with a new one and is discarded after the pretreatment reaction of each sample in order to prevent contamination by other samples. Therefore, when plural kinds of measurement are conducted with the one pretreatment reaction product, the pretreatment reaction should be repeated for each of the measurements, requiring a lager amount of the sample, or requiring longer time for the pretreatment, disadvantageously.

A sample which contains the objective substance of the measurement at a concentration exceeding the scale range of the measurement apparatus should be diluted before the measurement. In this case, the non-diluted sample is firstly subjected to measurement, then the sample is diluted manually or by use of a dilution device, and the diluted sample is subjected again to the measurement. The concentration is calculated by multiplying the measured value by the dilution factor. Otherwise, non-diluted samples are successively measured, and samples falling outside the measurable concentration range are diluted in an off-line process of the measurement apparatus and are measured again by inputting the dilution factor. Alternatively, samples found to be outside the measurable range are diluted on-line during the measurement to obtain the concentration by multiplication of the inputted dilution factor.

However, the dilution including manual dilution, and automatic dilution by an off-line process by the measurement apparatus requires operations of sample dilution, sample resetting, apparatus operation condition setting, and so forth, which cannot be automated, and requires longer time for measurement. Furthermore, with automatic preliminary on-line dilution by an analysis apparatus, although the dilution is conducted automatically and the measurement time is shortened, the measurement speed is still low disadvantageously.

It was considered by the inventors of the present invention that the above problems encountered in the prior art are caused by the practice of the pretreatment (including a pretreatment reaction and dilution) and measurement in the same measurement vessel in a measurement reaction system. For example, a measurement apparatus equipped with an automatic on-line dilution device comprises a pretreatment vessel for dilution or the like and a measurement incubator for immune reaction, enzyme reaction or the like in integration, and uses one cuvette for each measurement item for each sample. Such an apparatus requires repetition of the same dilution for each of plural measurements for one and the same sample.

Therefore, comprehensive studies have been made on an efficient automatic pretreatment device for dilution, pretreatment reaction, and other pretreatment.

SUMMARY OF THE INVENTION

An object of the present invention is to provide an automatic pretreatment device for conducting automatically and efficiently pretreatment such as dilution and pretreatment reaction by separating the measurement reaction system and the pretreatment system.

The automatic sample pretreatment device of the present invention comprises (1) a sample rack, (2) a pretreatment vessel and a measurement vessel, (3) a liquid dispensing mean, (4) a first vessel-transfer means having a vessel holder for holding and transferring the vessels, (5) a pretreatment vessel feeding means for feeding the pretreatment vessel to the vessel holder of the first vessel-transfer means, (6) a measurement vessel feeding means for feeding the measurement vessel to the vessel holder of the first vessel-transfer means, (7) a vessel discarding hole for discarding the vessel after use, (8) a second vessel-transfer means for transferring the used vessel held at the vessel holder of the first vessel-transfer means to the vessel discarding hole, (9) a incubator equipped with a measurement means for measuring a sample, and (10) a third vessel-transfer means for transferring the vessel held by the vessel holder of the first vessel-transfer means to the incubator, wherein (a) the sample rack holds a sample container containing a sample and a container containing a pretreatment reagent, (b) the liquid dispensing mean sucks a prescribed amount of the liquid from the container on the sample rack and discharges the prescribed amount of the sucked liquid into a vessel placed at a liquid discharge position on a carrying track of the first vessel-transfer means, and sucks and discharges the predetermined amount of the liquid from and to the vessel placed on the liquid discharging position, (c) the pretreatment vessel feeding means stores plural pretreatment vessels and feeds the vessel to the vessel holder placed at the pretreatment vessel feeding position on the carrying track of the first vessel-transfer means, (d) the measurement vessel feeding means stores plural measurement vessels, and feeds the vessel to the vessel holder placed at a measurement vessel feeding position on the carrying track of the first vessel-transfer means, (e) the second vessel-transfer means transfers the used vessel to the discarding hole placed at the vessel discarding position on the carrying track of the first vessel-transfer means, (f) the third vessel-transfer means transfers the vessel from the vessel transfer position on the carrying track of the first vessel-transfer means to a vessel receiving position on the incubator, (g) the incubator is provided with a measurement means for measuring a non-pretreated sample and/or a pretreated sample, and capable of holding at least one vessel, (h) the first vessel-transfer means has a vessel holder for holding and transferring the pretreatment vessel and/or the measurement vessel; and a carrying track for delivering the vessel holder capable of holding the pretreatment vessel and/or the measurement vessel, and connecting the liquid discharging position for the liquid dispensing mean, the pretreatment vessel feeding position for the pretreatment vessel feeding means, the measurement vessel feeding position for the measurement vessel feeding means, the vessel discarding position for the second transfer means, and the vessel transfer position for the third vessel-transfer means to transfer the vessel between the positions.

DETAILED DESCRIPTION OF THE PREFERRED EMBODIMENT

The present invention is described below in detail.

The present invention intends to provide an automatic sample pretreatment device of an automatic analysis apparatus. The pretreatment device of the present invention is employed in pretreatment such as pretreatment reaction and dilution of a sample in automatic measurement. For example, such pretreatment is necessary in a sandwich reaction or a competitive reaction in immunoassay. The measurement is conducted after automatic on-line pretreatment of the sample in a pretreatment reaction system separate from the main reaction system of the measurement.

Firstly, the pretreatment operation is explained about the dilution of a sample at a desired ratio, before the measurement, by use of the device of the present invention. A sample rack holds one or more containers containing respectively a sample to be measured, and a diluent container containing a diluent for sample dilution. The sample rack may further hold a reagent for the measurement as described later. Specific examples of the reagent include an enzyme substrate solution in immunoassay with an enzyme-labeled antibody or antigen, and a washing liquid for separation of bonded/free labeled substances. Plural kinds of diluents may be used for the sample dilution. The sample rack is not limited to be of a single structure, but may be constituted of two racks comprising a sample container rack and a diluent container rack. Any type of rack may be used which is capable of holding the aforementioned containers, and may be provided with a temperature-controlling mechanism such as a heater and/or a cooler for controlling the temperature of the sample in the container.

The sample rack may be placed on the same level as, or under the incubator described later. With the sample rack placed under the incubator, the floor space for the apparatus can be decreased, which is suitable for the application field such as clinical test application requiring a smaller apparatus.

The sample and the diluent in the containers placed on the sample rack are sucked and discharged by a liquid dispensing mean. An ordinary dispensing mean, which is constituted of a pump or an air cylinder and a nozzle, is useful therefor. The contamination of a sample by another samples and/or of a diluent by a sample is prevented preferably by using a disposable nozzle tip and replacing it with a new one automatically before sucking of a different kind of liquid. The liquid dispensing mean is not limited to be single, but may be provided in plurality: one liquid dispensing mean is used for sucking and discharging of both the sample and the diluent, or a liquid dispensing mean for the sample and the one for the diluent are provided separately. When an additional reagent is held on the sample rack as described above, the liquid dispensing mean may be used also for dispensation of the reagent.

When one liquid dispensing mean is used both for a sample and for a diluent, the sucking-discharging operation may be conducted separately for the sample and for the diluent, or the sucking-discharging of the sample and the diluent may be conducted in one operation. In the latter case, preferably the diluent is firstly sucked and subsequently the sample is sucked in order to prevent contamination of the diluent with the sample. Also in the case where the operation is conducted in two steps, preferably the diluent is firstly sucked and discharged and then the sample is sucked and discharged.

The liquid sucking from a sample container or another container may be conducted with a fixed sample rack by moving a liquid dispensing mean to an intended container position and inserting the nozzle tip or the like into the container, when a sufficient space can be secured around the sample rack. Thereby the construction of the sample rack can be simplified. In another example, the movement range of the liquid dispensing mean is limited, and the nozzle tip is inserted into the containers only at a fixed position on the sample rack. In this example, the sample rack and/or the liquid dispensing mean are combined with a driving means for driving the sample rack and/or the liquid dispensing mean in X-Y directions and a position-detecting means, whereby the liquid dispensing mean and/or the containers held by the sample rack are moved to the aforementioned predetermined position. In a still another example, a disk type of turntable is used as the sample rack, the containers are placed along a concentric circle on the turntable, and the liquid is sucked at a predetermined position of the circle. With this constitution, all the samples in the containers on the turntable can be sucked by rotating the turntable as the sample rack With the containers placed on plural concentric circles on the turntable of the sample rack, the samples can be sucked from a larger number of the containers by constructing the liquid dispensing mean to traverse all the concentric circles in a limited movement range of the liquid dispensing mean.

The liquid dispensing mean sucks a sample and a diluent and discharges the sample and the diluent into a vessel held on a vessel holder of a first vessel-transfer means. To the vessel holder of the first vessel-transfer means, pretreatment vessels or measurement vessels are fed from a pretreatment vessel feeding means or a measurement vessel feeding means. In the measurement without dilution, the measurement vessel is fed to the aforementioned holder by a measurement vessel feeding means, and the sample is introduced thereto. Then the succeeding operations are conducted. On the other hand, in the measurement with dilution, the pretreatment vessel is fed to the aforementioned holder by a pretreatment vessel feeding device, and the sample and the dilution liquid are introduced therein in a predetermined dilution ratio.

For uniform dilution of the sample with the diluent, preferably the liquid mixture in the pretreatment vessel is sucked and discharged repeatedly by the liquid dispensing mean, and then a prescribed amount of the diluted sample is sucked by the dispensing mean (first dilution operation). Otherwise, the uniform dilution can also be achieved by transferring the pretreatment vessel containing the sample and the diluent to the incubator provided with an agitation means, and agitating liquid in the pretreatment vessel.

When the vessel holder of the first vessel-transfer means capable of holding two or more vessels has a room for an additional vessel, the vessel holder is moved to a measurement vessel feeding means, a measurement vessel is transferred to the vessel holder, and then the diluted sample sucked by the nozzle is discharged into the measurement vessel to conduct the subsequent operations. On the other hand, when the vessel holder is capable of holding only one vessel, a pretreatment vessel holding a diluted sample is discarded by use of a second vessel-transfer means, the vessel holder is moved to the measurement vessel feeding means, the measurement vessel is transferred to the vessel holder, and the diluted sample sucked by the nozzle is discharged into the measurement vessel to conduct the subsequent operations.

If further dilution is necessary after the aforementioned first dilution, another pretreatment vessel is fed to the vessel holder instead of feeding a measurement vessel, and a predetermined amount of the diluted sample after the first dilution, and the diluent are introduced to the fed pretreatment vessel to conduct second dilution. In this second dilution, the diluent is sucked again from the diluent container on the sample rack. In the second dilution with one liquid dispensing mean, the tip of the nozzle end is preferably replaced with a new tip after the discharge of the diluted sample before a second dilution to prevent contamination of the diluent with the sample. By repeating the above dilution operation, the sample can be diluted to a desired dilution ratio. The sample diluted to a measurement concentration as above is sucked in a predetermined amount by the liquid dispensing mean, and the later operation is conducted with a measurement vessel.

In the present invention, even with a vessel holder for holding only one vessel, a sample can be diluted to any desired dilution ratio and can be measured by discarding a pretreatment vessel and feeding a new pretreatment vessel or a measurement vessel. In most measurement operations, one dilution operation of the sample is enough, and at least two vessels are used: one for pretreatment and the other for measurement. Therefore, the vessel holder is preferably capable of holding two or more vessels. More preferably the vessel holder is capable of holding two pretreatment vessels for two dilution operations and one measurement vessel (three vessels in total), or is capable of holding one vessel for pretreatment reaction, one vessel for dilution, and one vessel for measurement (three vessels in total). The vessel holder for two or more vessels may be set in a rectangular or parallel direction to the holder movement direction mentioned later.

As described above, the vessel holder of the first vessel transfer means is preferably capable of holding two or more vessels. The first vessel-transfer means may be constituted of two or more independent vessel holders, and the same number of independent carrying tracks as the number of the vessel holders.

When one or more vessel holders used are capable respectively of holding plural vessels, the vessel containing the finally diluted sample solution for the measurement and the vessel containing the solution of intermediate dilution ratio can be held during the dilution and measurement. Therefore, with such a vessel holder, even when the sample is over-diluted and the measurement should be conducted again, the dilution operation need not be repeated from the beginning, advantageously.

The aforementioned pretreatment vessel feeding means stores many pretreatment vessels, and feeds the pretreatment vessels to the vessel holder of the first vessel-transfer means. The measurement vessel feeding means stores many measurement vessels, and feeds the measurement vessels to the vessel holder of the first vessel-transfer means.

The measurement vessel is relatively expensive since the measurement vessel for the final measurement, optical measurement for example, is used or managed usually in consideration of influence of the non-uniformity of the construction material and shape of the vessel on the measurement results. On the other hand, the pretreatment vessel is not strictly limited, and is less expensive. It is profitable to use less expensive vessels as the pretreatment vessels which are used more in number than the measurement vessels and to use expensive vessels as the measurement vessels. Thus, the apparatus of the present invention is advantageous in that the kind of the vessel can be selected depending on the uses. In immunoassay, for example, the measurement vessel is often sealed with enclosure of a reagent such as an antibody, bonded to an insoluble carrier, against the objective measurement substance; an antibody, bonded to a labeling substance like an enzyme, against the objective measurement substance; and an additive for stabilizing the immune reaction. Such a sealed measurement vessel which does not serve as a pretreatment vessel can be used in the present invention. When the one and the same vessel is used for the pretreatment and the measurement, or when pretreatment vessels and measurement vessels are selectively fed, the pretreatment vessel feeding means and the measurement vessel feeding means need not be separately provided, but one vessel feeding means is sufficient for feeding the both kinds of vessels selectively. In the selective vessel feeding, a bar code reading device may be combinedly used for reading the bar code on the vessel. When different vessels are used for pretreatment dilution and pretreatment reaction mentioned later, the vessels are fed by the aforementioned selective vessel feeding means or by two vessel-feeding means in the apparatus of the present invention.

The pretreatment vessel and the measurement vessel used in the present invention are preferably in nearly the same shape to be readily caught by the second and the third vessel-transfer means, and to be holdable by the vessel holder of the first vessel-transfer means.

The second vessel-transfer means serves to discard the vessels held on the vessel holder of the first vessel transfer means after use for the measurement. The second vessel-transfer means catches the vessel on the vessel holder and transfer the vessel to the vessel-discarding hole. In the analysis of biological samples such as blood and serum, the vessels after the measurement hold a solution containing the sample. In such biological measurement, a waste matter storage chamber is preferably joined to the vessel discarding hole to prevent spill of the liquid contained in the discarded vessels. The waste matter storage chamber is preferably provided with a mechanism for sterilization such as a heating mechanism, as necessary.

The third vessel-transfer means serves to transfer the vessels from the vessel holder of the first vessel-transfer means to the incubator described later, and to transfer the vessels from the incubator to the holder of the first vessel transfer means. In the dilution treatment in most cases, the diluted sample is not transferred to the incubator, and this third vessel-transfer means is not employed in the dilution treatment. Instead, the diluted sample is introduced into the measurement vessel, and the measurement vessel is transferred to the incubator for measurement by this third vessel-transfer means. The third vessel-transfer means is also employed, in conducting a pretreatment reaction described later, for transferring a pretreatment incubator containing a mixture of a pretreatment reagent and a sample to the incubator, and re-transferring the vessel after the pretreatment reaction to the first vessel-transfer means.

The second vessel-transfer means and the third vessel-transfer means need not be provided separately, but may be combined into one vessel-transfer means, which may serve also to transfer the vessels from the holder of the first vessel-transfer means to the discarding hole, or may serve to transfer the vessels between the first vessel-transfer means and the incubator. The second vessel-transfer means may be constituted so as to transfer the measurement vessels on the incubator to the vessel discarding hole. With such a constitution, the vessels can be transferred from the first vessel-transfer means to the incubator, and the measurement vessel after the measurement can be discarded automatically.

The pretreatment vessel or the measurement vessel can be taken up by catching the flange of the vessel from upside by the vessel transfer means, or by clamping the vessel by two arms. The measurement vessel which has been sealed by a sealing material at the top opening with the aforementioned immune reaction reagents enclosed therein can be taken up by aspiration with an aspiration head. In using such a measurement vessel sealed with a sealing material, a breaker device is provided to break the seal material before the introduction of the sample. Naturally, the second vessel-transfer means and the third vessel-transfer means may be constructed so as to catch the pretreatment vessel or the measurement vessel by different mechanisms. The above vessel catching methods are applicable to the aforementioned pretreatment vessel feeding means and the measurement vessel feeding means.

The incubator is employed for causing the desired reaction and conducting the measurement with a diluted or undiluted sample. For example, in immunoassay, an antigen-antibody reaction is caused as the main reaction system, and the reaction result is measured. The incubator can be employed also for a pretreatment reaction as described below (for example, pretreatment by reaction of a sample with a pretreatment reagent such as a protein denaturing agent for a prescribed time). The incubator should be capable of holding at least one vessel, and is preferably capable of holding plural vessels for efficient pretreatment and measurement of a larger number of samples. For effective pretreatment reaction and other treatment, the incubator is preferably controllable automatically with a temperature sensor to be at a prescribed temperature by a heater or the like, or is placed in a thermostated box. Further the incubator is preferably provided with an agitation means for agitating the diluted sample, promoting the pretreatment reaction stably, and promotion of the main reaction such as immune reaction in immunoassay. The agitation means includes vibration agitation means such as ultrasonic agitation means and vibrational agitation means, stirring means of stirring directly the liquid in the vessel with a stirrer, and magnetic agitation means of agitating the liquid with a magnetic piece introduced preliminarily or in the pretreatment with movement of an external magnet. The magnetic agitation means is effective, for example, for an immune reaction measurement vessel in which a thermoplastic resin carrier containing a magnetic substance such as ferrite and having an antigen or an antibody immobilized thereon for the immune reaction.

The incubator is provided with a measurement means for measurement of a pretreated and/or non-pretreated sample. The non-pretreated sample herein signifies a sample which has been sucked from a sample container and discharged into a measurement vessel by means of a liquid dispensing mean and has not been subjected to pretreatment such as pH-adjustment and dilution.

The measurement means includes optical measurement means such as fluorometric analysis means, emission spectral analysis means, and absorption spectral analysis means; electrochemical measurement means such as conductivity measurement means; and immune sensor comprising an oscillator and an antigen or the like immobilized thereon, but is not limited thereto. Of these, the fluorometric analysis means and other optical measurement means are preferred for high-sensitivity measurement.

Any measurement means is applicable which is capable of conducting the above measurement of the sample placed on the incubator. For example, an optical measurement means for measuring fluorescence of a sample is constituted of a light emission system and a light receiving system: the light emission system comprising a light source, a filter for separating a desired wavelength light component from source light to excite the sample fluorometrically; and the light receiving system for fluorescence measurement comprising a filter for separating a desired wavelength component from fluorescent light from the sample, and a light-receiving element. These systems may be separated from the incubator, and are optically connected to the measurement vessel on the incubator through an optical fiber, a mirror, or the like. In particular, by use of a dichroic mirror, measurement can be conducted by projection of exciting light from the upside of the measurement vessel and receiving fluorescence light or the like above the measurement vessel. The details of the measurement means are selected depending on the main reaction system and the resulting signals. For example, in immunoassay employing an enzyme as the labeling substance, a fluorescence measurement system or a light emission measurement system is suitably selected depending on the relation between the enzyme and the substrate.

In the optical measurement, when measurement light is projected from the upside of the measurement vessel and the light transmitted through the sample and the measurement vessel is to be measured for light absorbance or the like at the side reverse to the light projection side, a small window is provided on the incubator for light transmission. Like this, the incubator may be constructed to serve as a part of the light path of the measurement means.

The measurement means may be made movable, for example, relative to the incubator for measurement of one or all of the plural measurement vessels on the incubator. For optical measurement, an example of the measurement means is a movable combination of an optical fiber for transmitting light from a light emitting system to the sample and another optical fiber for transmitting the light from the sample to a light receiving system. However, the constitution is preferred in which a measurement means is fixed, and an incubator is moved to bring a measurement vessel to the measurement position. In an example, a means for driving the incubator in X-Y directions and a position-detecting sensor means are combined to bring the measurement vessel on the incubator to the prescribed measurement position. In another example, the incubator is in a disk-shaped turntable, measurement vessels are placed on a concentric circle or circles, and the measurement is conducted at a prescribed position on the circle. Thereby, the samples in all of the measurement vessels on the circle can be measured by turning the disk-shaped incubator. When the measurement vessels are placed along plural concentric circles, the measurement means is designed to traverse all the circles, or a third vessel-transfer means is provided, in addition to the aforementioned constitution, to transfer the measurement vessels on any of the circles to the measurement position. Naturally, a separate vessel transfer means may be provided independently of the third vessel-transfer means.

To the incubator, the vessel is transferred by the third vessel-transfer means which may be integrated with the second vessel-transfer means or may be provided independently of the second vessel-transfer means. The third vessel-transfer means may be designed to transfer the vessel to any position on the incubator, or to transfer the vessel to a prescribed position only on the incubator. With the latter type third vessel-transfer means, the vessel transfer is controlled such that a vessel other than the intended vessel is not placed at the prescribed measurement position by employing a disk turntable type incubator, or other means. The measurement vessels after the measurement may be discarded by transferring firstly the measurement vessel to the vessel holder of the first vessel-transfer means by the third vessel-transfer means, and then transferring the vessel to the discarding hole by the second vessel-transfer means, or by employing additional vessel transfer means separately from the above vessel transfer means to transfer the vessel to the aforementioned discarding hole or another discarding hole.

The incubator may further be provided with an additional means in accordance with the measurement item of the sample. In enzyme immunoassay, for example, the additional means is exemplified by a dispensing mean serving for the aforementioned liquid dispensation as well as for enzyme substrate dispensation into the measurement vessels, or an independent dispensing mean, and one or two washing means for bonded/free reagent separation.

In the apparatus of the present invention, the liquid dispensing mean, the first vessel-feeding means, the second vessel-transfer means, and the third vessel-transfer means are combined functionally by the first vessel-transfer means. More specifically, the first vessel-transfer means is constituted of a vessel holder for holding the vessel, and a carrying track for carrying the vessel holder, and is capable of carrying the vessel along the carrying track. The vessel holder is constructed from a material, such as metals like aluminum and resins like acrylic resins, having a certain mechanical strength. The first vessel-transfer means carries the vessel holder to the position for liquid dispensation by the liquid dispensing mean, the positions for vessel feeding by the pretreatment vessel feeding means and the measurement vessel feeding means, the position for vessel catching by the second vessel-transfer means, and the position for vessel catching by the third vessel-transfer means, and connects these means. The vessel holder can be driven by a driving means constituted of a stepping motor and a timing belt.

A sensor may be provided for detecting the presence of the vessel at the vessel holder of the first vessel-transfer means to prevent failure in feeding or transferring the vessels. The sensor may be constituted of an optical detection means which projects detecting light upward through a hole punched at the recess of the holder for fitting the vessel.

In the apparatus of the present invention, a controller may be provided for controlling the movement of the respective means to conduct the operations of from the sample pretreatment to the measurement. A conventional microcomputer may be employed as the controller, and sensors may be provided for the respective means to confirm the operations.

The pretreatment reaction as the pretreatment is explained below. The basic constitution of the apparatus is described above. The sample rack holds one or more containers for the samples, and a container containing the pretreatment reagent to be used in the pretreatment reaction. The pretreatment reagent is not limited to one kind, but plural pretreatment reagents may be used. For example, for denaturation of protein of the sample as the pretreatment reaction, a hydroxide such as sodium hydroxide and potassium hydroxide, a cyanide such as sodium cyanide and potassium cyanide, or the like is employed. For reduction of a specific component in the sample as the pretreatment reaction, a reducing agent such as dithiothreitol and mercaptoethanol is employed. For pH adjustment of the sample in the pretreatment reaction, a buffer solution such as a phosphate buffer solution and an acetate buffer solution is employed. Various pretreatment reactions can be allowed to proceed: two or more of the above mentioned pretreatment reagents may be combined to cause parallel reactions; a reducing agent and an oxidation agent may be successively used; or an acidic buffer solution and an alkaline buffer solution may be successively used. For example, in the case where pH of a sample should be adjusted within a certain range as in enzyme immunoassay employing alkaline phosphatase for labeling an antibody or an antigen, the pH is adjusted for the pretreatment reaction by use of an alkaline or acidic buffer solution, and the pH is again adjusted finally.

The liquid dispensing mean sucks a sample and a pretreatment reagent, and discharges the sucked liquid into a vessel held by a vessel holder on the first vessel-transfer means. When the sample measurement is conducted without dilution or pretreatment reaction, a measurement vessel is fed to the vessel holder, the sample is dispensed thereto, and the subsequent operation is conducted. On the other hand, when a pretreatment reaction is conducted, a sample and a pretreatment reagent are introduced into a pretreatment vessel having been fed to the vessel holder by a pretreatment incubator feeding means. Then the sample and the pretreatment reagent are mixed, for example, by sucking and discharging the liquid in the pretreatment vessel, and the vessel containing the sample and the pretreatment reagent is transferred to a thermostated incubator provided with a stirring means or the like, if necessary, to allow the pretreatment reaction to proceed for a prescribed time.

The transfer of the vessel to the incubator for the pretreatment reaction can be conducted in the same manner as the transfer of the vessel in the dilution pretreatment by the third vessel-transfer means. Preferably, the mixture of the sample and the pretreatment reagent after the pretreatment reaction in the incubator is again transferred to the vessel holder of the first vessel-transfer means. The mixture may be mixed with another pretreatment reagent, or diluted as above, if necessary. In any case, necessary operations are conducted: including sucking and dispensing of the pretreatment reagent by the liquid dispensing mean, sucking and dispensing of a prescribed amount of the sample after the pretreatment reaction and the diluent, feeding of the pretreatment vessel to the first transfer means by the pretreatment vessel feeding means, and discarding of the vessel after the measurement by the second vessel-transfer means, and other operations. In the case where the pretreatment is completed by addition of one kind of pretreatment reagent, a prescribed amount thereof is sucked by the liquid dispensing mean, and a measurement vessel is fed to the first vessel-transfer means by the measurement vessel feeding means.

The operations of the respective means are similar to the aforementioned dilution treatment for the case where the vessel holder of the first vessel-transfer means is capable of holding two or more vessels, or holding only one vessel. Therefore, when not only dilution but also pretreatment reaction is conducted, or both dilution and pretreatment reaction is conducted as the pretreatment, the holder of the first vessel-transfer means is preferably designed to be capable of holding two or more vessels.

For the pretreatment reaction, the constitution is the same as above regarding the pretreatment vessel feeding means, the measurement vessel feeding means, the second vessel-transfer means, the third vessel transfer means, and the incubator. Particularly in the pretreatment reaction, the incubator is preferably equipped with a temperature control means and agitation means since temperature control and agitation are important in the pretreatment reaction.

The present invention gives following advantages: (1) Pretreatment of a sample can be conducted with plural pretreatment reagents and diluents, (2) Multiple dilution can be practiced, as necessary, to obtain a diluted sample liquid with a precise and high dilution factor, and (3) In repeated measurement of one sample after dilution and/or pretreatment reaction, necessary amounts of the sample fractions can be taken without pretreatment for each measurement, and so forth. The pretreatment device of the present invention may be integrated into a measurement apparatus such as immunoassay apparatus, so that all the measurement operations from the pretreatment including dilution and pretreatment reaction to the measurement can be automated.

The pretreatment apparatus of the present invention is described in more detail by reference to drawings without limiting the invention thereby.

Figure 1:
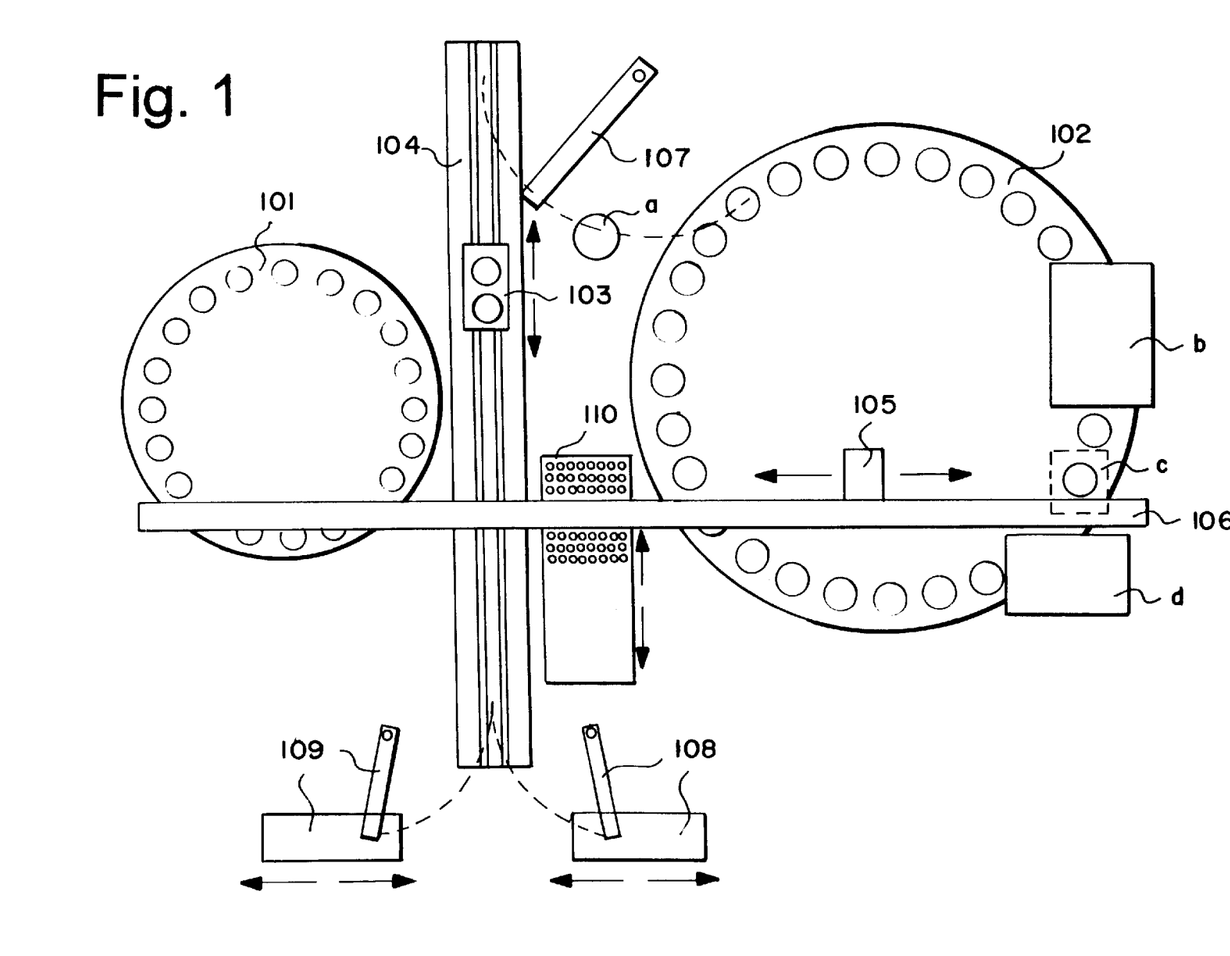
FIG. 1 illustrates an example of an automatic immunoassay apparatus equipped with the automatic sample pretreatment device of the present invention.

FIG. 1 illustrates constitution of an automatic immunoassay apparatus equipped with an automatic sample pretreating device of the present invention. In this example, a sample rack 101 and a incubator 102 are respectively in a form of a disk type turntable. Between the sample rack 101 and the incubator 102, there is provided a first vessel-transfer means comprising a vessel holder 103 for holding two vessels and a linear carrying track 104. The sample rack holds a sample container containing a sample, a diluent container containing a liquid for diluting the sample, a pretreatment reagent container containing a protein-denaturing agent for denaturing the protein in the sample, and a substrate container containing 4-methylumbelliferyl phosphate, a substrate for alkaline phosphatase. The sample rack is rotatable in a direction shown by the arrow mark.

A liquid dispensing mean is constituted of a nozzle 105 having a disposable tip 110 attached thereto and connected to an air cylinder not shown in the drawing, and a carrying track 106 for moving the nozzle between the sample rack and the incubator. The carrying track 106 of the liquid dispensing mean is extended to the incubator to dispense a solution of the substrate for the alkaline phosphatase held on the sample rack to a measurement vessel in the incubator in immunoassay. A vessel transfer means 107 serving as a second vessel-transfer means as well as a third vessel-transfer means is capable of transferring the vessel by circular movement between the end of the first vessel-transfer means and the incubator over a used vessel discarding hole a. The measurement vessel feeding means 108 and a pretreatment vessel feeding means 109 are capable of carrying vessels, by circular movement, from a measurement vessel storage chamber or a pretreatment vessel storage chamber not shown in the drawing to the end of the first vessel transfer means. In this example, the pretreatment vessel before the pretreatment is empty, and the measurement vessel holds a carrier of about 1.5 mm diameter having an antibody immobilized thereon and an antibody labeled by alkaline phosphatase in a freeze-dried state, or holds a carrier of about 1.5 mm diameter having an antibody immobilized thereon and an antigen labeled by alkaline phosphatase in a freeze-dried state. The carrier encloses ferrite therein, and content of the measurement vessel can be agitated by a magnet device equipped in the incubator. The measurement vessel is sealed with a sealing foil which will be broken on transfer of the vessel from the measurement vessel storage chamber to the first vessel-transfer means by a sealing foil breaker not shown in the drawing.

The incubator comprises a double-tube nozzle having a slit of about 1 mm wide for separating an enzyme-labeled antibody (or antigen) bonded indirectly to the carrier by immune reaction; a washing means b having a suction pump connected thereto and a washing liquid tank; a dispensing mean c for dispensing the alkaline phosphatase substrate solution; and a detection means d for detecting fluorescence of fluorescent substance (4-methylumbelliferone) formed by decomposition of the substrate by the alkaline phosphatase. The measurement vessel is transferred to the above means by rotation of the incubator itself in the arrow mark direction. In the pretreatment reaction of the sample, the incubator delivers the pretreatment vessel, rapidly by skipping the above means, to the position where the vessel is caught by the third vessel-transfer means 107. In this example, as shown in FIG. 1, the liquid dispensing mean serves also as the dispensing mean c for the alkaline phosphatase substrate solution. Under the incubator, a disk having the same diameter and holding magnets is provided to cause agitation of the reaction liquid by movement of the magnetic carrier in the incubator with rotation of the incubator.

Figure 2:
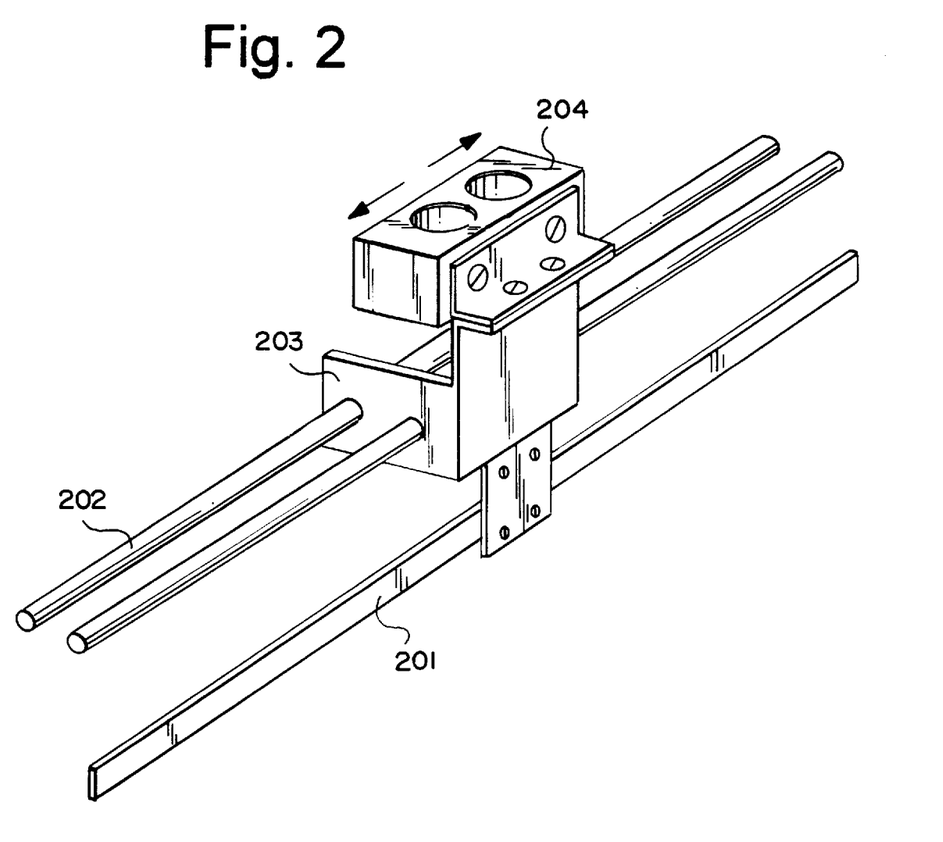
FIG. 2 illustrates the first vessel-transfer means of the automatic sample pretreatment device of an automatic immunoassay apparatus of the present invention.

FIG. 2 illustrates the first vessel-transfer means. This first vessel-transfer means is constituted of a carrying track comprising a timing belt 201 for transmitting a driving force from a motor not shown in the drawing and a carriage frame 203 travelling in the arrow mark directions along the a pair of parallel guide shafts 202; and a vessel holder 204 having cavities for holding two vessels. A detector is provided (not shown in the drawing) above and at the both ends of the guide shafts 202 to detect the position of the vessel holder 204 and the presence of the vessel on the vessel holder. Thereby, the vessel can be transferred precisely to the measurement vessel feed position, the pretreatment vessel feed position, the liquid dispensation positions, and vessel transfer positions by the second and third vessel-transfer means.

Figure 3:
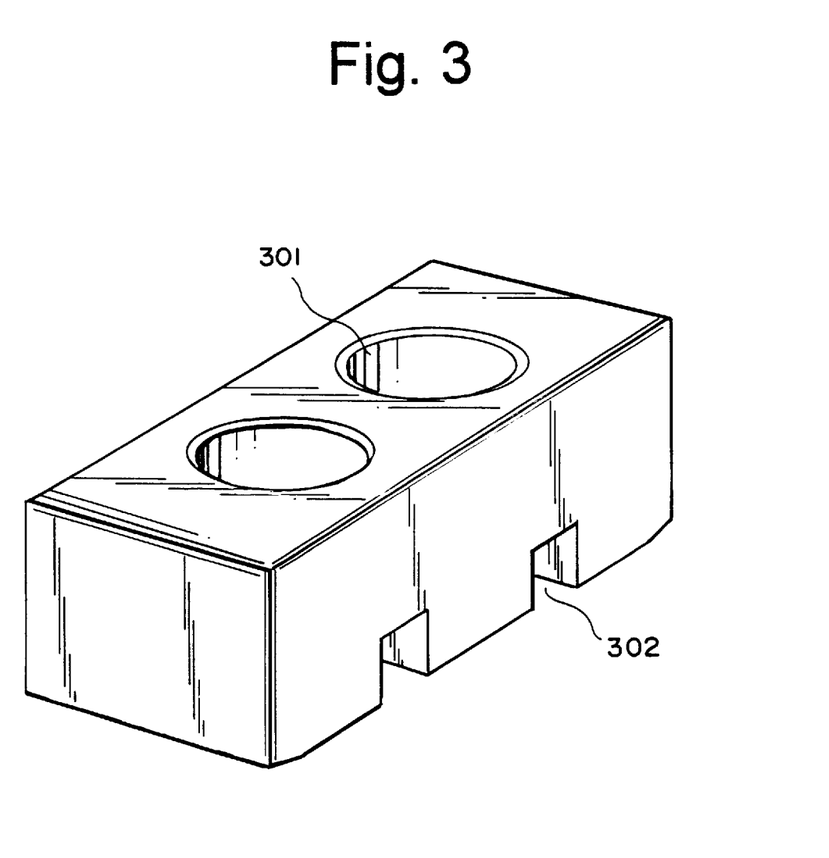
FIG. 3 illustrates of a vessel holder of the first vessel-transfer means of the automatic sample pretreatment device of the present invention for an automatic immmunoassay apparatus.

FIG. 3 shows the vessel holder of FIG. 2 in more detail. The vessel holder has two cavities 301 for holding two vessels, and a groove 302 at the bottom of the respective cavities for detecting the presence of the vessel.

The apparatus of the present invention as shown in FIG. 1 is manipulated with a control means not shown in the drawing as below:

(1) The liquid dispensing mean is moved to a predetermined position above the sample rack. Simultaneously, the sample rack is turned to bring the container containing the required diluent, or the pretreatment reagent to the position just below the liquid dispensing mean.

(2) The liquid dispensing mean is lowered at the aforementioned position to insert the end of the tip of the nozzle into the container. The dimensions of the containers are inputted to the control means to control the distance of the nozzle lowering so as not to bring the nozzle tip into contact with the bottom of the container. The lowering of the nozzle is stopped, and a prescribed amount of the liquid (diluent, and/or pretreatment reagent) is sucked into the nozzle. Then the nozzle is pulled up, and the sample rack is turned to bring the desired sample container to the position just below the aforementioned predetermined position. A prescribed amount of the sample is sucked into the nozzle in the same manner as above. When the pretreatment of the sample is not conducted, the above operation of suction of diluent and/or pretreatment reagent is omitted.

(3) Separately from the above operations, the first vessel-transfer means is driven to bring the vessel holder to the vessel feeding position of the pretreatment vessel feeding means to transfer the pretreatment vessel to the vessel holder. Then the vessel holder is moved to the crossing point of the carrying track 104 of the first vessel-transfer means and the carrying track 106 of the liquid dispensing mean. There the sample and the pretreatment reagent having been sucked into the nozzle tip as described above are discharged into the pretreatment vessel. The discharged liquid is agitated by sucking and discharging the liquid in the pretreatment vessel by the dispensing mean. In the case where the pretreatment of the sample is not conducted, the measurement vessel is used.

(4) The first vessel-transfer means is driven to bring the vessel holder to the position where the vessel is caught by the third vessel-transfer means. The pretreatment vessel is transferred by the third vessel-transfer means to the thermostated incubator to allow pretreatment reaction to proceed for a prescribe time. In the case where the pretreatment of the sample is not conducted, the immune reaction is caused, in the incubator, with an antibody immobilized on a carrier, an antibody bonded to the objective substance and an enzyme, or the like, and subsequently the measurement vessel is transferred to a washing means, a substrate-dispensing mean, and an optical measurement means by turning the incubator to conduct immunoassay. In another case where the sample need not be reacted for a certain time like simple dilution, this step is omitted and the operation of step (6) is conducted.

(5) After the pretreatment reaction for a prescribed time, the incubator is turned, and the pretreatment vessel is moved to the vessel-catching position of the third vessel-transfer means. The pretreatment vessel is transferred, by aid of the third vessel-transfer means, to the vessel holder of the first vessel-transfer means.

(6) For conducting additional pretreatment, the pretreatment vessel is transferred to the vacant cavity having no vessel, and another pretreatment reagent is introduced from the liquid dispensing mean to the pretreatment vessel as described above, and the pretreatment reaction is allowed to proceed in the incubator for a prescribed time. After this pretreatment reaction, the operations of the steps (5)–(7) are conducted. If the reaction in the incubator is not necessary as in simple dilution, the operations below are conducted. For the measurement, a measurement vessel is transferred to the vacant cavity of the vessel holder, and the vessel holder is moved to the crossing point of the carrying track of the first vessel-transfer means and the moving path of the liquid dispensing mean. There, the pretreated sample is sucked in a prescribed amount, and is discharged into the measurement vessel. When there is no vacant cavity in the vessel holder after the two pretreatment reactions, the first vessel-transfer means is driven to move the vessel holder to the vessel-catching position of the second vessel-transfer means, and the unnecessary pretreatment vessel is discarded through the discarding hole.

(7) In the measurement, the measurement vessel is transferred to the incubator as described above. There, the immune reaction is allowed to proceed with an antibody immobilized on a carrier, and an antibody bonded to the objective substance in the sample and an enzyme, or the like. Subsequently, the measurement vessel is transferred successively to a washing means, a substrate dispensing mean, and an optical measurement means by turning the incubator to conduct the immunoassay.

The results of the immunoassay is calculated by a microcomputer or the like not shown in the drawing, and are output by a display and a printer. With the apparatus shown in FIG. 1, so-called two step measurement (forward method) is practicable in which the measurement vessel contains only a freeze-dried antibody (or antigen); and an enzyme-bonded antibody (or antigen) is introduced into the incubator by a dispensing mean provided in the incubator; and separation is conducted twice. With the apparatus, still another measurement method is practicable in which an antibody bonded to a carrier, and an antibody bonded to an enzyme are introduced respectively into an empty measurement vessel by separate dispensing mean.

What is claimed is:

1. An automatic sample pretreatment device comprising (1) a sample rack, (2) a pretreatment vessel and a measurement vessel, (3) a liquid dispensing means, (4) a first vessel-transfer means having a vessel holder for holding and transferring the vessels, (5) a pretreatment vessel feeding means for feeding the pretreatment vessel to the vessel holder of the first vessel-transfer means, (6) a measurement vessel feeding means for feeding the measurement vessel to the vessel holder of the first vessel-transfer means, (7) a vessel discarding hole for discarding the vessel after use, (8) a second vessel-transfer means for transferring a used vessel held at the vessel holder of the first vessel-transfer means to the vessel discarding hole, (9) an incubator equipped with a measurement means for measuring a sample, and (10) a third vessel-transfer means for transferring the vessel held by the vessel holder of the first vessel-transfer means to the incubator, wherein (a) the sample rack holds a sample container containing a sample and a container containing a pretreatment reagent, (b) the liquid dispensing mean sucks a prescribed amount of the liquid from the container on the sample rack and discharges the prescribed amount of the sucked liquid into a vessel placed at a liquid discharging position on a carrying track of the first vessel-transfer means, and sucks and discharges the predetermined amount of the liquid from and to the vessel placed on the liquid discharging position, (c) the pretreatment vessel feeding means stores plural pretreatment vessels and feeds the vessel to the vessel holder placed at the pretreatment vessel feeding position on the carrying track of the first vessel-transfer means, (d) the measurement vessel feeding means stores plural measurement vessels, and feeds the vessel to the vessel holder placed at a measurement vessel feeding position on the carrying track of the first vessel-transfer means, (e) the second vessel-transfer means transfers the used vessel to the discarding hole placed at the vessel discarding position on the carrying track of the first vessel-transfer means, (f) the third vessel-transfer means transfers the vessel from the vessel transfer position on the carrying track of the first vessel-transfer means to a vessel receiving position on the incubator, (g) the incubator is provided with a measurement means for measuring a non-pretreated sample and/or a pretreated sample, and capable of holding at least one vessel, (h) the first vessel-transfer means has a vessel holder for holding and transferring the pretreatment vessel and/or the measurement vessel; and a carrying tract for delivering the vessel holder capable of holding the pretreatment vessel and/or the measurement vessel, said first vessel-transfer means connecting the liquid discharging position for the liquid dispensing means, the pretreatment vessel feeding position for the pretreatment vessel feeding means, the measurement vessel feeding position for the measurement vessel feeding means, the vessel discarding position for the second transfer means, and the vessel transfer position for the third vessel-transfer means to transfer the vessel between the positions.

2. The automatic sample pretreatment device according to claim 1, wherein the vessel holder of the first vessel-transfer means is capable of holding two vessels.

3. The automatic sample pretreatment device according to claim 1, wherein the vessel holder of the first vessel-transfer means is capable of holding three or more vessels.

4. The automatic sample pretreatment device according to claim 1, wherein the first vessel-transfer means is constituted of two or more independent vessel holders capable respectively of holding one or more vessels, and independent vessel carrying tracks each corresponding respectively to each of the vessel holders.

5. The automatic sample pretreatment device according to claim 1, wherein the incubator has function of controlling the temperature of the liquid in the vessel held therein.

6. The automatic sample pretreatment device according to claim 1, wherein the incubator has function of agitation for agitating the liquid in the vessel held therein.

7. The automatic sample pretreatment device according to claim 1, wherein the sample rack is a disk-shaped turntable, and is capable of holding the sample container and/or the container containing the pretreatment reagent along one and the same circle or different concentric circles.

8. The automatic sample pretreatment device according to claim 1, wherein the incubator is a disk-shaped turntable.

9. The automatic sample pretreatment device according to claim 1, wherein the pretreatment reagent is a diluent liquid, and the pretreatment is dilution of the sample.

10. The automatic sample pretreatment device according to claim 1, wherein the pretreatment reagent is a reagent for causing pretreatment reaction of the sample, and the pretreatment is a pretreatment reaction of the sample.

11. The automatic sample pretreatment device according to claim 1, wherein the pretreatment reagent includes a diluent and a pretreatment reagent for causing pretreatment reaction of the sample, and the pretreatment includes dilution of the sample and pretreatment reaction of the sample.

12. The automatic sample pretreatment device according to claim 1, wherein the liquid dispensing mean is movable in vertical and horizontal directions.

13. The automatic sample pretreatment device according to claim 1, wherein the vessel holder of the first vessel-transfer means is provided with a sensor for detecting the presence of the vessel on the vessel holder.

14. The automatic sample pretreatment device according to claim 1, wherein the measurement means is an optical measurement means constituted of a light emitting system and a light receiving system.

15. The automatic sample pretreatment device according to claim 1, wherein the measurement means conducts measurement for a measurement vessel placed at any position of the incubator.

* * * * *